(12) United States Patent
Fritsch et al.

(10) Patent No.: US 8,633,246 B2
(45) Date of Patent: Jan. 21, 2014

(54) OMEGA-3 FATTY ACIDS FOR OSTEOARTHRITIS

(75) Inventors: Dale A Fritsch, Topeka, KS (US);
Dennis E Jewell, Lawrence, KS (US);
William D Schoenherr, Hoyt, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 1726 days.

(21) Appl. No.: 10/912,864

(22) Filed: Aug. 6, 2004

(65) Prior Publication Data
US 2005/0043405 A1    Feb. 24, 2005

Related U.S. Application Data

(60) Provisional application No. 60/608,926, filed on Aug. 11, 2003.

(51) Int. Cl.
  A61K 31/20     (2006.01)
  A61K 31/201    (2006.01)
  A61K 31/202    (2006.01)
  A23K 1/18      (2006.01)

(52) U.S. Cl.
  USPC .......................................... 514/560; 424/442

(58) Field of Classification Search
  USPC .......................................... 514/560; 424/442
  See application file for complete search history.

(56) References Cited

U.S. PATENT DOCUMENTS

| | | | |
|---|---|---|---|
| 3,683,076 A | 8/1972 | Rovati | |
| 4,843,095 A | 6/1989 | Rubin | |
| 4,895,725 A | 1/1990 | Kantor et al. | |
| 5,364,845 A | 11/1994 | Henderson | |
| 5,434,183 A | 7/1995 | Larsson-Backstrom | |
| 5,776,913 A | 7/1998 | Ogilvie et al. | |
| 5,840,715 A | 11/1998 | Florio | |
| 5,843,919 A | 12/1998 | Burger | |
| 5,916,565 A | 6/1999 | Rose et al. | |
| 6,015,798 A | 1/2000 | Ogilvie et al. | |
| 6,136,795 A | 10/2000 | Florio | |
| 6,162,787 A | 12/2000 | Sorgente et al. | |
| 6,297,280 B1 | 10/2001 | Ishihara et al. | |
| 6,331,567 B1 | 12/2001 | Watson et al. | |
| 6,344,220 B1 | 2/2002 | Rose et al. | |
| 6,399,105 B1 | 6/2002 | Collin | |
| 6,426,100 B2 * | 7/2002 | Watkins et al. | 426/2 |
| 6,432,929 B1 | 8/2002 | Stone | |
| 6,485,752 B1 | 11/2002 | Rein | |
| 6,552,081 B1 | 4/2003 | Freedman et al. | |
| 6,593,099 B2 | 7/2003 | Xiao et al. | |
| 6,638,525 B2 | 10/2003 | Weidner | |
| 6,645,948 B2 | 11/2003 | Petito et al. | |
| 2001/0044425 A1 | 11/2001 | Ekanayake | |
| 2001/0051184 A1 | 12/2001 | Heng | |
| 2001/0051206 A1 | 12/2001 | Hayek et al. | |
| 2002/0001640 A1 | 1/2002 | Watkins et al. | |
| 2002/0018828 A1 | 2/2002 | Lepine | |
| 2002/0068098 A1 | 6/2002 | Babish et al. | |
| 2002/0068718 A1 | 6/2002 | Pierce | |
| 2002/0076452 A1 | 6/2002 | Babish et al. | |
| 2002/0077299 A1 | 6/2002 | Babish et al. | |
| 2002/0164386 A1 | 11/2002 | Meisner | |
| 2003/0124219 A1 | 7/2003 | Bui et al. | |
| 2003/0147971 A1 | 8/2003 | Myers | |
| 2004/0068010 A1 | 4/2004 | Zicker et al. | |
| 2005/0057718 A1 | 3/2005 | Chen et al. | |
| 2006/0024356 A1 | 2/2006 | Waldron et al. | |
| 2006/0105931 A1 | 5/2006 | Shi et al. | |

FOREIGN PATENT DOCUMENTS

| | | |
|---|---|---|
| AU | 2002311777 | 10/2002 |
| CN | 1557451 | 12/2004 |
| EP | 0678247 | 10/1995 |
| EP | 0713653 | 5/1996 |
| JP | 2006-528950 | 12/2006 |
| RU | 2112534 | 6/1998 |
| WO | WO 97/09982 | 3/1997 |
| WO | WO 97/21434 | 6/1997 |
| WO | WO 99/04782 | 2/1999 |
| WO | WO 00/21524 | 4/2000 |
| WO | WO 01/60356 | 8/2001 |
| WO | WO 01/82720 | 11/2001 |
| WO | WO 03/075670 | 9/2003 |
| WO | WO 2004/006688 | 1/2004 |
| WO | WO 2005/018630 | 3/2005 |
| WO | WO 2005/117603 | 12/2005 |
| WO | WO 2006/002976 | 1/2006 |

OTHER PUBLICATIONS

Bierer, et al, Improvement of Arthritic Signs in Dogs Fed Green-Lipped Mussel (*Perna canaliculus*), *J. Nutri.* 132:1634S-1636S, 2002.
Caterson, et al., Mechanisms involved in cartilage proteoglycan catabolism, *Matrix Biology* 19:333-344, 2000.
Curtis, C.L. et al., Effects of n-3 fatty acids on cartilage metabolism, *Proc. Of Nutr. Soc.*, 61:381-389, 2002.
Curtis, C.L., Biological basis for the benefit of nutraceutical supplementation in arthritis, *Drug Discovery Today*, 9:4, 165-172, 2004.
Hansen, R.A., N-3 fatty acids decrease inflammatory mediators in arthritic dogs, *FASEB J.* 17:A330 (Abstract #200.3), 2003.
Kremer, J.M., et al, Effects of Manipulation of Dietary Fatty Acids on Clinical Manifestations of Rheumatoid Arthritis, *The Lancet*, 184-187, Jan. 26, 1985.
Kremer, J.M., n-3 Fatty acid supplements in rheumatoid arthritis, *Am J Clin Nutr*, 71(suppl):349S-351S, 2000.

(Continued)

*Primary Examiner* — Sreeni Padmanabhan
*Assistant Examiner* — Jody Karol
(74) *Attorney, Agent, or Firm* — Thomas M. Hunter

(57) ABSTRACT

Methods for restoring a more nearly normal joint function in an osteoarthritic dog and methods for decreasing the likelihood of a dog developing osteoarthritis involve administering to the dogs a composition containing an effective concentration of the omega-3 fatty acid, eicosapentaenoic acid (EPA).

13 Claims, No Drawings

(56) References Cited

OTHER PUBLICATIONS

Lands, W.E., Biochemistry and physiology of n-3 fatty acids, *The FASEB Journal* 6:2530-2536m 1992.

Miller WH, et al., Treatment of dogs with hip arthritis with a fatty acid supplement. *Canine Practice* 17(6): 6-8, 1992.

Nesbitt, GH, et al, Effect on n-3 fatty acid ratio and dose on clinical manifestations, plasma fatty acids and inflammatory mediators in dogs with pruritus, *Verterinary Dermatology*, 14:67-74, 2003.

Richardson, D.C., et al., *Vet. Clin. North Amer. Small Animal Practice* 27:883-911, 1997.

Schoenherr, W.D., et al. In *Small Animal Clinical Nutrition 4th Ed.*, Hand et al. Eds., Walsworth Publishing Company, Marceline, MO, 907-921, 2000.

Volker, D., et al, Efficacy of Fish Oil Concentrate in the Treatment of Rheumatoid Arthritis, *The Journal of Rheumatology*, 27:2343-2346, 2000.

Volker, D.H., et al., The Eicosapentaenoic to Docosahexaenoic Acid Ratio of Diets Affects the Pathogenesis of Arthritis in Lew/SSN Rats, *Am. Soc. For Nutr. Sci.*, 559-565, 2000.

Miller et al., 1989, "Clinical Trial of DVM Derm Caps in the Treatment of Allergic Disease in Dogs: A Nonblinded Study," J. Amer. Animal Hospital Assoc. 25(2):163-168.

Adam, 2003, "Dietary fatty acids and immune reactions in synovial tissue," European Journal of Medical Research 8(8):381-387.

Adan et al., 1999, "Effects of docosahexaenoic and eicosapentaenoic acid on lipid metabolism, eicosanoid production, platelet aggregation and atherosclerosis in hypercholesterolemic rats," Bioscience, Biotechnology and Biochemistry 63(1):111-119.

Beale, 2004, "Use of nutraceuticals and chondroprotectants in osteoarthritic dogs and cats," Vet. Clin. North Amer. Small Anim Pract. 34(1):271-289.

Bierer, 2002, "Improvement of arthritic signs in dogs fed green-lipped mussel (*Perna canaliculus*)," J. Nutr. 132(6 Suppl. 2):1634S-1636S.

Borras et al., 1999, "Age-related changes in the brain of the dog," Vet. Pathol. 36(3):202-211.

Brigelius-Flohe et al., 1999, "Vitamin E. Function and Metabolism," FASEB J. 13:1145-1155.

Budsberg, 2002, "Effects of fatty acid supplementation on the development of osteoarthritis in dogs: biochemical, clinical and radiographic evaluation," Abstracts of the 1st World Orthopaedic Vet. Congress, Munich, pp. 56-57.

Bui et al., 2001, "Influence of green lipped mussels (*Perna canaliculus*) in alleviating signs of arthritis in dogs," Vet. Ther. 2(2):101-111.

Calder et al., 2001, "Polyunsaturated fatty acids and rheumatoid arthritis," Curr. Opin. Clin. Nutr. Metab. Care 4(2):115-121.

Cao et al., 1998, "Increases in Human Plasma Antioxidant Capacity after Consumption of Controlled Diets High in Fruit and Vegetables," Amer. J. Clin. Nutr. 68:1081-1087.

Chin et al., 1990, "Effect of lipoxygenase products on glycosaminoglycan (GAG) synthesis by cultured chondrocytes," Clin. Rheumatol. & Related Res. 3(4):265-271.

Clemmons, 1997, "Research Support for Degenerative Myelopathy," Degenerative Myelopathy Funding, U. of FL College of Vet Med. Http://neuro.vetmed.ufl.edu/neuro/DM_Web/Funding.htm.

Cummings et al., 1996, "The Canine As an Animal Model of Human Aging and Dementia," Neurobiol. Of Aging 17:259-268.

Curtis et al., 2003, "The effect of n-3 (omega-3) polyunsaturated fatty acids on degenerative joint disease," Database FSTA Online! International Food Information Service AN: 2003-00-a2058 Abstract; Agro Food Industry Hi Tech 14(3):61-69.

De Vizia et al., 2003, "Effect of an 8-month treatment with omega-3 fatty acids (eicosapentaenoic and docosahexaenoic) in patients with cystic fibrosis," Journal of Parenteral and Enteral Nutrition 27(1):52-57.

Frei, 1999, "Molecular and Biological Mechanisms of Antioxidant Action," FASEB J. 13:963-964.

Fujimoto et al., 1989, "The effect of dietary docosahexaenoate on the learning ability of rats," in: Health Effects of Fish and Fish Oils, Chandra, ed., ARTS Biomedical Publishers and Distributors, St. John's, Newfoundland, pp. 275-284.

Geels et al., 2000, "Evaluation of a High N-3 Fatty Acid Diet for the Treatment of Degenerative Joint Disease of the Canine Stifle," Vet Surgery ACVS Abstracts, 29(5):462 Abstract #30.

Hagen et al., 1999, "(R)-alpha-lipoic acid-supplemented old rats have improved mitochondrial function, decreased oxidative damage, and increased metabolic rate," FASEB J. 13(2):411-418.

Hansen et al., 2003, "N-3 fatty acids decrease inflammatory mediators in arthritic dogs," Exp. Biol.: Translating the Genome, Abstract #3146, San Diego, CA.

Harman, 1993, "Free Radical Theory of Aging: A Hypothesis on Pathogenesis of Senile Dementia of the Alzheimer's Type," Age 16:23-30.

Head et al., 1995, "Spatial Learning and Memory as a Function of Age in the Dog," Behavioral Neurosci. 109(5):851-858.

Hedbom et al., 2002, "Molecular aspects of pathogenesis in osteoarthritis: the role of inflammation," Cell Mol. Life Sci. 59:45-53.

International Search Report and Written Opinion in International Application No. PCT/US04/025759, mailed Dec. 7, 2004.

International Search Report and Written Opinion in International Application No. PCT/US06/004858, mailed Mar. 6, 2007.

James et al., 1997, "Dietary n-3 fatty acids and therapy for rheumatoid arthritis," Seminars in Arthritis and Rheumatism 27(2):85-97.

Jones et al., 1997, "Evidence for the involvement of docosahexaenoic acid in cholinergic stimulated signal transduction at the synapse," Neurochemical Research 22(6):663-670.

Leveque, 1998, "Cognitive Dysfunction in Dogs, Cats an Alzheimer's-Like Disease," J. Amer. Vet. Med. Assoc. 212(9):1351.

Lovell et al., 1998, "Elevated 4-Hydroxynonenal in Ventricular Fluid in Alzheimer's Disease," Neurobiol. Of Aging 18:457-461.

Markesbery et al., 1998, "Four-Hydroxynonenal, a Product of Lipid Peroxidation, Is Increased in the Brain in Alzheimer's Disease," Neurobiol. Of Aging 19:33-36.

McGahon et al., 1999, "Age-related changes in oxidative mechanisms and LTP are reversed by dietary manipulation," Neurobiology of Aging 20(6):643-653.

McGahon et al., 1999, "Age-related changes in synaptic function: analysis of the effect of dietary supplementation with omega-3 fatty acids," Neuroscience 94(1):305-314.

Milgram et al., 1994, "Cognitive Functions and Aging in the Dog: Acquisition of Nonspatial Visual Tasks," Behavioral Neurosci. 108(1):57-68.

Milgram et al., 1999, "Landmark Discrimination Learning in the Dog," Learning & Memory 6(1):54-61.

Mueller et al., 2003, "A retrospective study regarding the treatment of lupoid onychodystrophy in 30 dogs and literature review," J. Amer. Animal Hospital Assoc. 39(2):139-150.

National Research Council, 2006, Nutrient Requirements of Dogs and Cats, pp. 359-360.

Poole, 1999, "An introduction to the pathophysiology of osteoarthritis," Front. Biosci. 4:D662-670.

Reisbick et al., 1997, "Omega-3 fatty acidy deficiency and behavior," Chapter 17 in Handbook of Essential Fatty Acid Biology: Biochemistry, Physiology and Behavior Neurobiology, pp. 397-426.

Rogers, 2001, "A healthy body, a healthy mind: long-term impact of diet on mood and cognitive function," Proceedings of the Nutrition Society 60(1):135-143.

Saito et al., 1983, "In vitro effect of EPA on the metabolism of [1-$^{14}$C] arachidonic acid in rat peritoneal macrophages," The 2nd Department of Internal Medicine, School of Medicine, Chiba University, Chiba 280, Japan 623:162-170.

Sano et al., 1997, "A Controlled Trial of Selegiline, Alpha-Tocopherol, or Both as Treatment for Alzheimer's Disease. The Alzheimer's Disease Cooperative Study," New England J. Med. 336(17):1216-1222.

Schoenherr et al., 1997, "Nutritional modification of inflammatory diseases," Seminars in Veterinary Medicine and Surgery (Small Animal) 12(3):212-222.

Stammers et al., 1989, "Fish oil in osteoarthritis," Lancet 2(8661):503.

(56) References Cited

OTHER PUBLICATIONS

Tomobe et al., 2000, "Dietary docosahexaenoic acid suppresses inflammation and immunoresponses in contact hypersensitivity reaction in mice," Lipids 35(1):61-69.
Van Haaster et al., 1993, "Formation of prostanoids and hydroxy fatty acids by stimulated peritoneal mast cells: role of the dietary fat type in rat," Biochimica et Biophysica Acta. 1167(2):147-154.
Volker, 2000, "The eicosapentaenoic to docosahexaenoic acid ratio of diets affects the pathogenesis of arthritis in Lew/SSN rats," J. Nutr. 130(3):559-565.
Wander et al., 1997, "The ratio of dietary (n-6) to (n-3) fatty acids influences immune system function, eicosanoid metabolism, lipid peroxidation and vitamin E status in aged dogs," J. Nutr. 127(6):1198-1205.
Weaver et al., 1988, "Health effects and metabolism of dietary eicosapentaenoic acid," Prog. Food Nutr. Sci. 12(2):111-150.
www.DRNANCYSPLACE.COM/myelopathy.htm, 2007.
www.ETHICALNUTRIENTS.COM/au/content/products/fish-oil, 2008.
Youdim et al., 2000, "Essential fatty acids and the brain: possible health implications," Int. J. Devel. Neurosciences 18(4-5):383-399.
Richardson et al. "Nutritional Management of Osteoarthritis," Vet. Clinics of North America: Small Animal Practice, Jul. 1997, 27(4):883-911.

* cited by examiner

OMEGA-3 FATTY ACIDS FOR OSTEOARTHRITIS

CROSS REFERENCE TO RELATED APPLICATION

This application claims priority to U.S. Provisional Application No. 60/608,926 (filed Aug. 11, 2003). U.S. Provisional Application No. 60/608,926 is incorporated in its entirety by reference.

BACKGROUND

Osteoarthritis is a degenerative joint disease commonly occurring in humans and in companion animals (Richardson et al., *Vet. Clin. North Amer. Small Animal Practice* 27:883-911, 1997; Curtis et al., *Drug Disc. Today* 9:165-172, 2004). The disease involves progressive deterioration of articular cartilage with minimal inflammation (Schoenherr et al. in *Small Animal Clinical Nutrition* $4^{th}$ *Ed.*, Hand et al. Eds., Walsworth Publishing Company, Marceline, Mo., 2000, 907-921; Hedbom et al., *Cell Mol. Life Sci* 59:45-53, 2002; Pool, *Front Biosci* 4:D662-70, 1999). Management of osteoarthritis can include pharmacological treatments, surgery, nutraceutical administration and diet management. Such current management approaches have, however, focused on symptomatic relief and as such, they have not been entirely successful in disease management or in treating the underlying pathologies. Hence, there remains a continuing need for new approaches in managing osteoarthritis in humans and companion animals.

SUMMARY

Accordingly, the inventors herein have succeeded in discovering that administration of an effective amount of omega-3 fatty acids, in particular, Eicosapentaenoic acid (EPA) can provide a new approach for management of osteoarthritis in dogs. The methods are effective in managing osteoarthritis in dogs.

Thus, in various embodiments, the present invention can include methods for restoring a more nearly normal joint function in an dog having osteoarthritis. The methods can comprise feeding to the dog a composition comprising EPA at a concentration of at least about 0.2% by weight or a concentration of at least about 0.3% by weight.

The present invention can also include methods for decreasing the likelihood of a dog developing osteoarthritis. The methods can comprise feeding to the dog a composition comprising EPA at a concentration of at least about 0.2% by weight or a concentration of at least about 0.3% by weight.

The methods of the present invention method for decreasing the likelihood of a dog developing osteoarthritis can similarly comprise feeding to the dog a composition on the basis of the composition comprising a fatty acid component comprising a joint-function restoring amount of EPA.

The present invention can also include methods for decreasing the likelihood of a dog developing osteoarthritis and methods for restoring a more nearly normal joint function in an osteoarthritic dog comprising administering to the dog a composition comprising EPA in amount of about 37.5 mg/kg body weight, about 56.25 mg/kg body weight, about 75 mg/kg body weight or about 93.75 mg/kg body weight. Such compositions can be comprised by an animal food composition, an animal treat or an animal supplement.

The present invention can also include methods for decreasing the likelihood of a dog developing osteoarthritis and methods for restoring a more nearly normal joint function in an osteoarthritic dog comprising administering to the dog a composition comprising EPA in amount of about 37.5 mg/kg body weight, about 56.25 mg/kg body weight, about 75 mg/kg body weight or about 93.75 mg/kg body weight. Such compositions can be comprised by an animal food composition, an animal treat or an animal supplement.

In various embodiments, the methods for restoring a more nearly normal joint function in an osteoarthritic dog can involve treating the osteoarthritic disease or reducing symptoms of the disease in the dog and the methods for decreasing the likelihood of a dog developing osteoarthritis can involve preventing development of the osteoarthritic disease in a dog or preventing or diminishing the appearance of symptoms of the disease in the dog.

The methods of the present invention can additionally be based upon compositions that further comprise omega-6 fatty acids in a total amount of not more than about 3% by weight and/or a ratio of omega-6 fatty acids to omega-3 fatty acids of about 0.2 to about 1.1 and or a ratio of omega-6 fatty acids to EPA of about 1.0 to about 12.5.

DETAILED DESCRIPTION

This present invention can involve administration of omega-3 fatty acids, in particular, EPA in managing osteoarthritic diseases and symptoms of such diseases in mammals and in particular, in dogs.

Omega-3 fatty acids also known as n-3 fatty acids, are a recognized group of polyunsaturated fatty carboxylic acids, In general, the omega-3 fatty acids contain 12-26 carbon atoms with methylene-interrupted double bonds. The physiologically more important omega-3 fatty acids are 18-22 carbons in length and straight chained. The n-3 fatty acids have a double bond between the 3 and 4 carbon atoms as measured from the methyl end of the molecule. Eicosapentaenoic acid (EPA), Docosahexaenoic acid (DHA) and alpha-linolenic acid (ALA) are important n-3 fatty acids for managing osteoarthritis in mammals and EPA is particularly important in managing osteoarthritis in dogs. Derivatives of omega-3 fatty acids can also be used in managing osteoarthritis. Many types of derivatives are well known to one skilled in the art. Examples of suitable derivatives are esters, such as branched or unbranched and/or saturated or unsaturated $C_1$-$C_{30}$ cycloalkyl esters, in particular $C_1$-$C_6$ alkyl esters of omega-3 fatty acids, particularly EPA.

The omega-3 fatty acids, and in particular EPA, can be administered to a mammal, and in particular, to a dog, by any of many routes of administration, such as, for example, oral, intranasal, intravenous, subcutaneous and the like. The oral route is particularly suitable and EPA can be administered orally in a wet or dry diet, either incorporated therein or on the surface of any diet component, such as, by spraying, agglomerating, dusting or precipitating on the surface. It can be present in the nutritional diet per se or in a snack, supplement or a treat. It can also be present in the liquid portion of the diet such as water or another fluid. The EPA can be administered as a powder, solid or as a liquid including a gel. If desired the EPA can be orally administered in a nutraceutical or pharmaceutical dosage form such as a capsule, tablet, caplet, syringe, and the like. Within the dosage form the EPA can be present as a powder or a liquid such as a gel. Any of the usual neutraceutical or pharmaceutical carriers can be employed such as water, glucose, sucrose and the like together with the EPA.

In certain embodiments, the present invention can involve EPA-diet compositions that are essentially free of DHA and/ or ALA. Essentially free of DHA or ALA or mixtures thereof is intended to mean that either or both of DHA and ALA are substantially absent or that there are only small insignificant amounts of either or both of DHA or ALA present, for example, less than about 0.1%, less than about 0.03%, less than about 0.01%, less than about 0.03% or less than about 0.001%. In embodiments that are essentially free of DHA and/or ALA, any amount of DHA and/or ALA present is at a concentration sufficiently low so that no substantial effect is produced in an osteoarthritic dog on the disease of osteoarthritis, on the progression of osteoarthritis or on symptoms produced by the osteoarthritis.

The Omega-3 fatty acids and, in particular, EPA are effective against various forms of osteoarthritis as well as other forms of arthritis including rheumatoid arthritis.

The omega-3 fatty acid, EPA acts to prevent the development of the degenerative process in joint cartilage or to diminish the degenerative process and thereby improve joint in osteoarthritic dogs or in dogs that might otherwise develop osteoarthritis. This effect is in addition to an anti-inflammatory action of omega-3 fatty acids, which may be of less importance in canine osteoarthritis because a limited involvement of inflammation in the osteoarthritis.

Use of an in vitro explant procedure involving articular knee cartilage as shown in the examples below, demonstrated that EPA was the only omega-3 fatty acid to significantly decrease induced release of glycosaminoglycan (GAG) from the cartilage. With respect to prevention of joint damage from osteoarthritis a particular target group of pets, especially canines, are those that would be in need of such preventative care as opposed to the general population. For example, pets, particularly large breed canines such as Labrador retriever, Rottweiler, German shepherd and the like are more susceptible to osteoarthritis as demonstrated by its greater occurrence in these pets. Additionally, pets above the age of six (6) years, particularly dogs, have a significantly greater occurrence of osteoarthritis. EPA can be additionally useful in treating canines and felines with osteoarthritis. Also present with the EPA can be other omega-3 fatty acids such as DHA and ALA as well as omega-6 fatty acids, all of which can be found in sources such as fish oils in relatively large quantities.

The quantity of EPA which should be employed can vary substantially As shown in later examples, an actual dose response is observed—the greater the EPA, the greater the anti-arthritic effect. Generally, a minimum of at least about 0.2 wt % based upon the quantity of a nutritious diet satisfying ordinary requirements of a canine or feline on a daily basis. For example, a specific amount can be employed in the usual nutrient food ration on a daily basis or the same daily quantity can be provided to the animal in a treat or supplement on a daily basis. Additionally, a combination of these methods or any other dosing means can be employed as long as the effective quantity of EPA is provided. The range of amounts of EPA includes at least about 0.2%, at least about 0.25%, at least about 0.30%, at least about 0.4%, at least about 0.5%, at least about 0.6% up to about 2%, up to about 2.25%, up to about 2.5%, up to about 3%, up to about 4%, or up to about 5% on a Weight basis. It should be noted that all wt % are on a dry matter basis (DMB). EPA is an omega-3 fatty acid. Generally, the ratios of the EPA or omega-3 to omega-6 fatty acid can vary significantly. In various embodiments, the omega-6: omega-3 ratio can be from about 1.10 to 0.2 omega-6 to 1.0 omega-3 or from about 1.08 to 0.42 omega-6 to 1.0 omega-3 and more particularly, about 0.2, about 0.25, about 0.3, about 0.4, about 0.5, about 0.6, about 0.8, about 1.0, or greater. In various embodiments, the omega-6 to EPA ratio can be about 12.5 to about 1.0 omega-6 to 1.0 EPA, or about 12.4 to 1.12 omega-6 to 1.0 EPA and more particularly, about 0.2, about 0.25, about 0.3, about 0.4, about 0.5, about 0.6, about 0.8, about 1.0, about 1.5, about 2.0, about 2.5, about 3, about 4, about 5, about 6, about 7.5, about 10, about 12.5 or greater. The arachidonic acid, AA, (an omega-6) to EPA ratio can be about 0.28 to about 0.01 AA to 1.0 EPA to about 0.28 to 0.08 AA to 1.0 EPA.

The omega-3 fatty acid, and in particular EPA, can be administered in amounts calculated as mg/kg body weight. Thus for example, a 20 kg dog would be expected to consume about 275 g of diet per day. Amounts of EPA in the diet of about 0.2%, about 0.3%, about 4%, about 0.5% or about 0.6% by weight would amount to administering to the dog about 27.5 mg/kg body weight, about 41.25 mg/kg body weight, about 55 mg/kg body weight, about 68.75 mg/kg body weight or about 82.5 mg/kg body weight respectively. More particularly, EPA can be administered in an amount of about 20 mg/kg body weight, about 28 mg/kg body weight, about 30 mg/kg body weight, about 40 mg/kg body weight, about 41 mg/kg body weight, about 50 mg/kg body weight, about 55 mg/kg body weight, about 60 mg/kg body weight, about 69 mg/kg body weight, about 70 mg/kg body weight, about 80 mg/kg body weight, about 82 mg/kg body weight, about 90 mg/kg body weight, about 100 mg/kg body weight, about 120 mg/kg body weight, about 150 mg/kg body weight, or greater.

As indicated above, the EPA can be in the form of a food provided to the pet. Examples of such foods are regular diets providing all of the animal's nutrients, treats, supplements and the like. The EPA can be provided in liquids or in pharmaceutical dosage forms such as capsules, tablets, pills, liquids or even parenterally administered such as through syringe. The most important aspect is that the pet be provided an effective amount of EPA to prevent or treat the osteoarthritis. In various embodiments, the route of administration can be oral and the EPA can be incorporated into a food. Foods are generally classified in the pet food industry as "wet" or "dry". A wet food has a relatively high amount of water and is usually present in a can or a container wherein air is substantially or totally excluded. Examples of such foods are "chunk and gravy", individual solid particles in the presence of a liquid gravy or a loaf type material which generally takes the shape of the receptacle. The dry food is generally a baked or preferably extruded material, the latter then cut into individual shaped portions, usually known as kibbles. EPA is readily incorporated into a wet food through conventional means. Encapsulation can be employed to protect the EPA from air oxidation in a dry diet. Additionally, use of antioxidants and nitrogen sweeps of packaging can also be employed. This is exemplified by U.S. Pat. No. 4,895,725 which has special emphasis on the micro-encapsulation of specific fish oils. Oils which have high levels of omega-3 fatty acids, are menhaden, salmon, cod and the like.

The present invention also includes, in various embodiments, methods involving the administration of a composition comprising EPA for reducing the severity and frequency of clinical signs of osteoarthritis and the pain associated with this disease without substantial adverse reactions or side affects. Additionally, in various embodiments, the present invention provides a method of slowing the clinical progression of the osteoarthritic condition of the animal. There is also provided, in various embodiments, a method which substantially improves the overall osteoarthritic condition of the animal so that this benefit can be objectively measured through increased weight bearing in osteoarthritic limbs. The present invention also provides methods involving the administration of EPA in combination with other treatment modalities for osteoarthritis including the administration of various medicaments and/or feeding the animal a weight management diet both of which are known in the art.

Example 1

This example illustrates the release of glycosaminoglycan elicited by omega-3 fatty acids in cultured canine cartilage tissue.

Articular cartilage was obtained from left and right stifles (both femoral condyles and tibial plateau) of dogs. Cartilage explants cultured for 3 days in medium with 10% fetal bovine serum, then washed 3 times in serum free medium. Explants then cultured for 6 days in serum free medium containing 0, 100 or 300 µg/ml n3 fatty acid (EPA, ALA or DHA). After this period in fatty acid medium, all explants were washed 3 times in fatty acid free/serum free medium. Explants were then cultured individually for 4 days in 1 ml of fatty acid and serum free medium containing no additives (C), $10^{-6}$ M retinoic acid (RA) or 50 ng/ml oncostatin M (OSM). Note that not all treatments were possible on all dogs because of cartilage availability. The release of proteoglycan into the medium (µg/mg wet weight) was measured at the termination of culture. In the tables below, the mean and standard deviation of glycosaminoglycan (GAG) release for the triplicate cultures for each of the 4 dogs are given. In addition, the media lactate (µg/mg wet weight) concentrations were given for each treatment.

TABLE 1*

| Dog 1 Treatment | GAG Mean | GAG Std Dev | n | GAG Min | GAG Max | Lactate Mean | Lactate Std Dev |
|---|---|---|---|---|---|---|---|
| C | 1.363 | .497 | 3 | .849 | 1.84 | 26.07 | 33.7 |
| C + carrier | 1.630 | .306 | 3 | 1.31 | 1.92 | 21.95 | 22.6 |
| C + 100 EPA | 1.590 | .291 | 3 | 1.29 | 1.87 | 23.85 | 25.4 |
| C + 300 EPA | 1.036 | .528 | 3 | .57 | 1.61 | NA** | |
| RA | 10.497 | 1.837 | 3 | 8.89 | 12.5 | 36 | 39.3 |
| RA + carrier | 7.15 | 4.527 | 3 | 2. | 10.5 | 33.067 | 45.4 |
| RA + 100 EPA | 8.677 | 1.999 | 3 | 6.61 | 10.6 | 29.367 | 34.8 |
| RA + 300 EPA | 1.593 | 1.696 | 3 | .436 | 3.54 | 26.4 | 39.1 |
| OSM | 13.6 | 1.562 | 3 | 12.6 | 15.4 | 25.367 | 30.8 |
| OSM + carrier | 14.25 | 6.44 | 3 | 7.35 | 20.1 | 27.4 | 33.8 |
| OSM + 100 EPA | 6.293 | 2.301 | 3 | 4.34 | 8.8 | 33.567 | 52.5 |
| OSM + 300 EPA | 2.167 | 1.93 | 3 | .93 | 4.39 | 20.05 | 23.8 |

*GAG = glycosaminoglycan; C = serum free medium containing no additives, EPA = eicosapentaenoic acid; RA = retinoic acid; OSM = oncostatin M.
**not analyzed.

As shown in Table 1, significant decrease in GAG release occurred with 100 µg/ml EPA in OSM treated cultures and with 300 µg/ml in RA and OSM treated cultures. There was no significant decrease in media lactate concentrations with any dose of EPA.

TABLE 2*

| Dog 2 Treatment | GAG Mean | GAG Std Dev | n | GAG Min | GAG Max | Lactate Mean | Lactate Std Dev |
|---|---|---|---|---|---|---|---|
| C + carrier | .503 | .422 | 3 | .127 | .96 | 22.8 | NA |
| C + 100 EPA | .340 | .333 | 3 | .1 | .72 | 39.523 | 24.568 |
| C + 300 EPA | .573 | .46 | 3 | .250 | 1.1 | 39.2 | 13.865 |

TABLE 2*-continued

| Dog 2 Treatment | GAG Mean | GAG Std Dev | n | GAG Min | GAG Max | Lactate Mean | Lactate Std Dev |
|---|---|---|---|---|---|---|---|
| OSM + carrier | 11.7 | 5.11 | 3 | 7.1 | 17.2 | 26.9 | 4.766 |
| OSM + 100 EPA | 5.25 | 3.002 | 3 | 2.19 | 8.19 | 21.7 | 9.838 |
| OSM + 300 EPA | 2.83 | .229 | 3 | 2.66 | 3.09 | 16.233 | 3.602 |
| C + carrier | .973 | .222 | 3 | .84 | 1.23 | 17.4 | NA |
| C + 100 DHA | .640 | .312 | 3 | .45 | 1 | 21 | 6.265 |
| C + 300 DHA | .843 | .361 | 3 | .43 | 1.1 | 36.2 | NA |
| OSM + carrier | 8.73 | .777 | 3 | 8.1 | 9.6 | 25.333 | 7.106 |
| OSM + 100 DHA | 8.567 | 4.219 | 3 | 3.7 | 11.2 | 28.133 | 2.715 |
| OSM + 300 DHA | 6.073 | 4.029 | 3 | 3.18 | 10.7 | 24.8 | 1.947 |
| C + carrier | .821 | .684 | 3 | .193 | 1.55 | 15.567 | 1.955 |
| C + 100 ALA | 1.12 | .089 | 3 | 1.05 | 1.22 | 28.4 | 13.718 |
| C + 300 ALA | .993 | 1.104 | 3 | .14 | 2.24 | 41.667 | 14.958 |
| OSM + carrier | 7.81 | 7.471 | 3 | .26 | 15.2 | 51.7 | 28.488 |
| OSM + 100 ALA | 8.497 | 4.356 | 3 | 4.09 | 12.8 | 28.8 | 4.957 |
| OSM + 300 ALA | 6.42 | 2.730 | 3 | 3.44 | 8.8 | 55.233 | 30.305 |

*GAG = glycosaminoglycan; C = serum free medium containing no additives, EPA = eicosapentaenoic acid; RA = retinoic acid; OSM = oncostatin M.

As shown in Table 2, EPA but not ALA or DHA significantly decreased GAG release in OSM treated cultures. There was no significant effect on media lactate concentration by any dose of any of the fatty acids.

TABLE 3*

| Dog 3 Treatment | GAG Mean | GAG Std Dev | n | GAG Min | GAG Max | Lactate Mean | Lactate Std Dev |
|---|---|---|---|---|---|---|---|
| C + carrier | 2.727 | .867 | 3 | 2.01 | 3.69 | 26.33 | 4.366 |
| C + 100 ALA | 2.117 | .428 | 3 | 1.81 | 2.61 | 24.4 | 3.995 |
| C + 100 DHA | 1.903 | .826 | 3 | 1.28 | 2.84 | 29.35 | 5.728 |
| C + 100 EPA | 1.673 | .409 | 3 | 1.3 | 2.11 | 36.1 | NA |
| C + 300 ALA | 2.447 | .321 | 3 | 2.14 | 2.18 | 20.75 | 7 |
| C + 300 DHA | 1.55 | .73 | 3 | .73 | 2.13 | 28.4 | .566 |
| C + 300 EPA | 1.567 | .387 | 3 | 1.3 | 2.01 | 10.525 | 10.854 |
| RA + carrier | 20.823 | .653 | 3 | 20.1 | 21.37 | 38.467 | 4.782 |
| RA + 100 ALA | 20.44 | .903 | 3 | 19.4 | 21.02 | 43.233 | 2.281 |
| RA + 100 DHA | 21.093 | 6.881 | 3 | 13.38 | 26.6 | 45.667 | 8 |
| RA + 100 EPA | 16.223 | 6.654 | 3 | 8.61 | 20.93 | 41.533 | 2.515 |
| RA + 300 ALA | 24.467 | 2.987 | 3 | 21.1 | 26.8 | 44.753 | 4.821 |
| RA + 300 DHA | 19.457 | 2.389 | 3 | 17.28 | 22 | 47.967 | 9.139 |
| RA + 300 EPA | 1.537 | .618 | 3 | 1.08 | 2.24 | NA | NA |
| OSM + carrier | 12.773 | 5.845 | 3 | 6.36 | 17.8 | 37.867 | 11.547 |
| OSM – 100 ALA | 22.033 | 4.596 | 3 | 18.4 | 27.2 | 32.767 | 1.815 |
| OSM – 100 DHA | 11.667 | 6.007 | 3 | 5.5 | 17.5 | 32.267 | 11.467 |
| OSM – 100 EPA | 17.85 | 2.051 | 3 | 16.4 | 19.3 | 39.05 | 11.526 |
| OSM – 300 ALA | 23.467 | 3.102 | 3 | 20.3 | 26.5 | 34.033 | 1.38 |
| OSM – 300 DHA | 11.630 | 5.069 | 3 | 6.79 | 16.9 | 30.0 | 5.963 |
| OSM – 300 EPA | 8.1 | 6.767 | 3 | 3.79 | 15.9 | 21.467 | 1.93 |

*GAG = glycosaminoglycan; C = serum free medium containing no additives, EPA = eicosapentaenoic acid; RA = retinoic acid; OSM = oncostatin M.

As shown in Table 3, none of the fatty acids significantly altered GAG release from RA- or OSM-stimulated cartilage in this particular animal. There was no change in media lactate associated with any dose of any fatty acid.

TABLE 4*

| Dog 4 Treatment | GAG Mean | GAG Std Dev | n | GAG Min | GAG Max | Lactate Mean | Lactate Std Dev |
|---|---|---|---|---|---|---|---|
| C + carrier | 1.96 | .533 | 3 | 1.51 | 2.55 | 22.933 | 4.75 |
| C + 100 ALA | 2.103 | .107 | 3 | 1.98 | 2.17 | 20.533 | 3.478 |
| C + 100 DHA | 2.343 | .331 | 3 | 2 | 2.66 | 19.1 | 2.352 |
| C + 100 EPA | 2.687 | .996 | 3 | 1.72 | 3.71 | 23 | 6.183 |
| C + 300 ALA | 1.533 | 1.244 | 3 | .13 | 2.5 | 29.167 | 22.074 |
| C + 300 DHA | 2.307 | .361 | 3 | 1.93 | 2.65 | 24.933 | 3.4 |
| C + 300 EPA | 2.1 | .455 | 3 | 1.64 | 2.55 | 24.767 | 13.004 |
| RA + carrier | 14.113 | 3.89 | 3 | 9.64 | 16.7 | 34.533 | 12.368 |
| RA + 100 ALA | 12.547 | 6.348 | 3 | 5.94 | 18.6 | 39.933 | 11.594 |
| RA + 100 DHA | 11.28 | 7.123 | 3 | 4.79 | 18.9 | 25.6 | 11.766 |
| RA + 100 EPA | 14.393 | 2.9 | 3 | 11.23 | 16.93 | 32.967 | 4.219 |
| RA + 300 ALA | 14.093 | 6.138 | 3 | 8.98 | 20.9 | 59.367 | 31.166 |
| RA + 300 DHA | 11.3 | 6.815 | 3 | 3.5 | 16.1 | 25.333 | 11.684 |
| RA + 300 EPA | 9.093 | 1.316 | 3 | 8.26 | 10.61 | 25.1 | 4.67 |
| OSM + carrier | 16.083 | 3.544 | 3 | 12.05 | 18.7 | 31.2 | 5.991 |
| OSM + 100 ALA | 11.7 | 2.19 | 3 | 9.43 | 13.8 | 26.333 | 9.25 |
| OSM + 100 DHA | 24.967 | 3.262 | 3 | 21.2 | 26.9 | 36.833 | 5.066 |
| OSM + 100 EPA | 15.883 | 4.316 | 3 | 11.95 | 20.5 | 27.237 | 6.34 |
| OSM + 300 ALA | 19.557 | 3.909 | 3 | 15.5 | 23.3 | 26.667 | 6.099 |
| OSM + 300 DHA | 16.4 | 6.27 | 3 | 9.4 | 21.5 | 36.233 | 20.342 |
| OSM + 300 EPA | 13.493 | 5.752 | 3 | 7.54 | 19.02 | 27.8 | 2.722 |

*GAG = glycosaminoglycan; C = serum free medium containing no additives, EPA = eicosapentaenoic acid; RA = retinoic acid; OSM = oncostatin M.

As shown in Table 4, EPA at 300 µg/ml, but not any other fatty acid at any dose, significantly decreased GAG release from RA treated cultures. There was a significant decrease in media lactate concentration in control. RA- and OSM-treated cultures with the 300 µg/ml OSM pre-treatment.

Example 2

This example illustrates the incorporation of n-3 fatty acids into canine chondrocyte membranes.

The majority of these experiments were performed using monolayer cultures, however, in a single experiment, the incorporation of fatty acids into explant cultures of canine cartilage was analyzed.

Monolayer Cultures

Over 24 or 48 hours there was no incorporation of the 18:3 n-3 fatty acid ALA into chondrocyte membranes from two dogs. The % 18:3 n-3 in chondrocytes incubated in medium alone was <1 out of 5 (range=0.3-0.9%) and after 24 or 48 hours of incubation with 100 or 300 µg/ml ALA this percentage had not significantly changed (range=0.3-2.5%).

Over 48 hours there was significant incorporation of the 20:5 n-3 fatty acid EPA into chondrocyte membranes from one dog. The % 20:5 n-3 increased from <1% (range=0.2-0.6%) to approximately 7% (range=5.6-8%) when cultures were treated with 100 or 300 µg/ml EPA for 48 hours. The incorporation was not different when cultures were performed in the presence or absence of 5% FCS.

Over 48 hours there was significant incorporation of the 20:5 n-3 fatty acid EPA but not the 18:3 n-3 fatty acid ALA into chondrocyte membranes from one dog (doses of 300 µg/ml for each fatty acid). The % 20:5 n-3 increased from <1% to approximately 15%.

Over 3 or 6 days there was significant incorporation of the 20:5 n-3 fatty acid EPA into chondrocyte membranes from one dog (dose of 300 µg/ml EPA). The % 20:5 n-3 increased from <1% to 16-18% with no difference between 3 and 6 days incubation.

Explant Culture

Over 6 days there was apparent incorporation of the 20:5 n-3 fatty acid EPA, but not the 18:3 n-3 DHA or the n-6 fatty acid AA (arachadonic acid) into cartilage explants from one dog (dose of 300 µg/ml for each fatty acid). The % n-3 20:5 increased from 0% (none detectable) to approximately 2%.

These data indicated that EPA, but no other n-3 fatty acid was incorporated into canine chondrocyte membranes in either monolayer or explant cultures.

Example 3

This example illustrates the effect of n-3 Fatty Acids on Canine Chondrocyte Metabolism.

To assess the potential effect of n-3 fatty acids on protein and proteoglycan metabolism in canine cartilage, cultures were set up as described in Example 1 except for the final 4 days of culture, no catabolic stimuli were added (i.e., all "control" cultures). During the final 24 hours of culture (1) $^{35}SO_4$, or (ii) $^{35}$S-methionine and $^{35}$S-cysteine, were added to the medium to radiolabel newly synthesized proteoglycans and proteins, respectively. The incorporation of radiolabel into the cartilage matrix was measured at the termination of culture. No attempt was made to quantitate loss of radiolabelled material from the cartilage over the 24-hour labeling period. The mean and standard deviation of the incorporation of $^{35}SO_4$ ("PG") or $^{35}$S-methionine and $^{35}$S-cysteine ("PROT") as DPM/mg wet weight are shown in Table 5 below,

TABLE 5*

| Treatment | PG Mean | PG Std Dev | N | PROT Mean | PROT Std Dev |
|---|---|---|---|---|---|
| Carrier | 292.667 | 53.144 | 3 | 574.333 | 198.336 |
| 100 ALA | 246.333 | 100.779 | 3 | 503.667 | 184.218 |
| 100 DHA | 156.0 | 82.529 | 3 | 503.667 | 81.365 |
| 100 EPA | 537.333 | 161.81 | 3 | 442.0 | 72.746 |
| 300 ALA | 443.0 | 205.385 | 3 | 393.667 | 34.962 |
| 300 DHA | 123.333 | 38.24 | 3 | 564.333 | 220.048 |
| 300 EPA | 275.667 | 161.661 | 3 | 504.0 | 44.542 |

*PG = incorporation of $^{35}SO_4$ in DPM/mg wet weight; PROT = incorporation of $^{35}$S-methionine and $^{35}$S-cysteine as DPM/mg wet weight; EPA = eicosapentaenoic acid; DHA = docosahexaenoic acid; ALA = alpha-linolenic acid.

As shown in Table 5, there was no significant effect of any n-3 fatty acid on protein synthesis and incorporation into the matrix. EPA at 100 µg/ml significantly increased proteoglycan synthesis and incorporation. No other dose or fatty acid significantly altered proteoglycan synthesis and incorporation into the cartilage matrix.

Reverse transcription-PCR was used to measure the mRNA message expression levels of matrix proteinases (aggrecanases-1 and -2), cyclooxygenases-1 & -2, lipoxygenases-5 and 12, and potential autocrine cytokines and their receptors (e.g. IL-1, IL-6 and TNF).

The results of this study found that aggrecanase-1 and aggrecanase-2 mRNA messages were expressed in "normal" canine cartilage tissue. In addition, some dogs expressed mRNA message of cyclooxygenase-2 (COX-2) message although there were no signs of joint pathology in these animals. This enabled monitoring the effects of n-3 and n-6 fatty acid supplementation on mRNA expression of aggrecanases and COX-2 in unstimulated canine articular cartilage explants. EPA was the only fatty acid able to reduce the mRNA message for the degradative enzymes, aggrecanase-1 and aggrecanase-2, in canine articular cartilage. This demonstrated the ability of EPA to "turn off" the genes responsible for cartilage degradation.

Example 4

This study illustrates the effects of omega-3 fatty acids in canine osteoarthritis clinical studies.

Three clinical studies were conducted in pet dogs clinically diagnosed with osteoarthritis. Veterinary general practitioners and orthopedic specialists enrolled client owned dogs that met a specific eligibility criteria. All patients were required to: have radiographic evidence of osteoarthritis with measurable clinical manifestations of disease, based on historical accounts by pet owners and physical examinations by veterinarians; be otherwise healthy and free of concurrent diseases based on physical exam, CBC, blood chemistry, and urinalysis; maintain regimen of therapy if receiving medications or supplements prescribed for osteoarthritis during the 30 days prior to enrolling in the study.

The following measurements were made.

Serum fatty acid profile: This was determined by a gas chromatography method involving extraction of fatty acids by chloroform and methanol mixture (2:1), methylation using boron trifluride-methanol ($BF_3$:MeOH) reagent followed by flame ionization detection (FID). Fatty acid methyl esters were identified by comparison of retention times with those of known standards and quantitated using an internal standard.

Veterinary clinical evaluation: Veterinarians conducted both a physical exam and a clinical evaluation of the patient's osteoarthritic condition during the screening phase and at the conclusion of each of the feeding intervals over the course of the clinical trial. Veterinarians assessed the severity of five osteoarthritic parameters: lameness, reluctance to bear weight, reduction in range of motion, reluctance to hold up contra-lateral limb, and pain on palpation of the joint. Changes in severity scores for these individual parameters were measured over the duration of the feeding period. A comprehensive veterinary clinical assessment of the impact of dietary intervention on the osteoarthritic condition of patients was derived by combining the changes in severity scores for all five individual parameters.

Pet owner subjective evaluation: Pet owners were required to complete an enrollment questionnaire prior to participating in the study and additional questionnaires at the conclusion of each of the feeding intervals over the course of the clinical trial.

Enrollment questionnaire—pet owners rated the observed frequency and severity of the most common signs of canine osteoarthritis including difficulty rising from rest, limping, stiffness, soreness when touched, lagging behind during walks, yelping or whimpering in pain, aggressive behaviors, difficulty in running, difficulty in walking, difficulty in climbing steps, difficulty in jumping, difficulty in playing, impaired mobility, and overall activity level. In addition, owners rated the overall osteoarthritic condition of their pet.

Feeding questionnaire—pet owners rated both the frequency and change in severity of the signs of canine osteoarthritis which were benchmarked during enrollment. In addition, the pet owners rated the severity of their animal's pain associated with osteoarthritis.

Force plate gait analysis: Dogs were evaluated at each respective institution using a computerized biomechanics force plate at day 0, 6 weeks, and 12 weeks. The plate was mounted centrally in and flush with the surface of a 10 m walkway. A handler trotted dogs across the force plate and an observer evaluated each pass across the plate to confirm footstrikes and gait. A trial was considered valid if there were distinct ipsilateral fore foot and hind foot strikes while the dog was trotted across the force plate at a velocity of 1.7 to 2.0 m/s, with an acceleration variation of −0.5 to 0.5 $ms^2$. During each trial, the dog's forward velocity was measured, using a millisecond timer and two photoelectric switches. Each trial was videotaped for review and confirmation of valid foot-strikes. Care was taken to ensure that the dog triggered the timer and that a consistent speed (as perceived by the handler and observer) was maintained across the plate during each trial.

Five valid trials for each test period were obtained for each affected limb and each ipsilateral limb of each dog. Orthogonal ground reaction forces of peak vertical force, vertical impulse, braking and propulsive peak forces, and braking and propulsion impulses were measured and recorded by a specialized software program. (Acquire, Sharon Software, DeWitt, Mich.), All forces were normalized with respect to body weight in kilograms. Data from the valid trial for each limb were averaged to obtain a mean value for each force or impulse at each time period.

Ground reaction force data were compared between treatment and placebo groups as a percentage difference between lame and ipsilateral limbs at each time period. Percentage change of ground force data on the lame limb were compared at the beginning and end of the feeding period.

Study #1

A canine study was conducted to evaluate the dietary effect of feeding high levels of n-3 fatty acids to dogs diagnosed with osteoarthritis. Eighteen veterinary general practitioners were recruited to enroll patients in the study. A total of 131 dogs were randomly assigned to two dietary treatments and fed for 180 days. The test and control foods had similar macronutrient profile, but were significantly different fatty acid composition (Table 6). The test diet contained high levels of ALA, EPA, and DHA, and was formulated with a low n-6 n-3 ratio. The control diet was a leading selling commercially available dog food, with typical levels of n-3 fatty acids and n-6/n-3 ratio characteristic for the industry.

TABLE 6*

| Dietary Nutrient | Control Food (%) | Test Food (%) |
|---|---|---|
| Protein | 23.2 | 19.9 |
| Fat (total) | 13.9 | 13.6 |
| $CHO_2$ (NFE) | 54.7 | 53.3 |
| C18:3 n-3 (ALA) | 0.12 | 2.8 |
| C20:4 n-6 (AA) | 0.03 | 0.06 |
| C20:5 n-3 (EPA) | <0.01 | 0.38 |
| C22:6 n-3 (DHA) | <0.01 | 0.31 |
| Sum n-6 | 1.99 | 2.53 |
| Sum n-3 | 0.09 | 3.48 |
| n6/n3 ratio | 22.8 | 0.7 |

*NFE = Soluble carbohydrate content as Nitrogen Free Extract; ALA = alpha-linolenic acid; AA = arachidonic acid; EPA = eicosapentaenoic acid; DHA = docosahexaenoic acid.

Serum fatty acids and pet owner evaluations were recorded at 0, 45, 90 and 180 days. Serum fatty acid profiles were significantly modulated by the test food. The test group had significantly higher concentrations of n-3 fatty acids (P<0.01), specifically EPA, DHA, a-ALA, significantly lower concentrations of AA (P<0.01), and significantly lower n-6:n-3 ratios (P<0.01) as compared to the control group at the conclusion of each feeding interval (Table 7). The test group showed significant improvements for rising from rest, running, and playing at day 45 and walking at days 90 and 180 as compared to the control group based on pet owner observations (P<0.05), even in the presence of a strong placebo effect (Table 8).

TABLE 7*

Canine Mean Serum Fatty Acid Levels (mg/dl)

| | Group | Day 0 | Day 45 | Day 90 | Day 180 |
|---|---|---|---|---|---|
| C18:3 n-3 (α - ALA) | Control | 1.10 | 0.89 | 0.52 | 0.53 |
| | Test | 1.05 | 5.61 | 6.51 | 7.13 |
| C20:4 n-6 (AA) | Control | 71.35 | 66.34 | 68.03 | 68.21 |
| | Test | 64.32 | 45.90 | 46.13 | 42.65 |
| C20:5 n-3 (EPA) | Control | 1.14 | 0.90 | 0.67 | 0.93 |
| | Test | 1.28 | 16.28 | 18.64 | 19.94 |
| C22:6 n-3 (DHA) | Control | 2.67 | 2.03 | 1.70 | 1.98 |
| | Test | 2.93 | 11.31 | 12.24 | 12.17 |
| Sum n-6 | Control | 141.08 | 138.72 | 137.85 | 140.28 |
| | Test | 130.85 | 118.87 | 128.71 | 123.99 |
| Sum n-3 | Control | 4.95 | 3.84 | 2.93 | 3.51 |
| | Test | 5.36 | 33.20 | 37.39 | 39.24 |
| n-6:n-3 ratio | Control | 33.33 | 37.95 | 51.59 | 51.39 |
| | Test | 33.90 | 7.47 | 8.63 | 6.92 |

*ALA = alpha-linolenic acid; AA = arachidonic acid; EPA = eicosapentaenoic acid; DHA = docosahexaenoic acid.*

TABLE 8*

Pet Owner Observed Change in Severity of Osteoarthritis*

| Osteoarthritic Sign | Group | Day 0-45 Mean | P Value | Day 45-90 Mean | P Value | Day 90-180 Mean | P Value |
|---|---|---|---|---|---|---|---|
| Rising from rest | Control | 1.77 | .041 | 1.77 | nsd** | 1.93 | nsd** |
| | Test | 1.56 | | 1.84 | | 1.91 | |
| Running | Control | 1.81 | .037 | 1.83 | nsd** | 1.94 | nsd** |
| | Test | 1.56 | | 1.71 | | 1.91 | |
| Walking | Control | 1.71 | nsd** | 2.00 | .018 | 2.19 | .002 |
| | Test | 1.69 | | 1.71 | | 1.75 | |
| Playing | Control | 1.83 | .008 | 1.90 | nsd** | 2.06 | nsd** |
| | Test | 1.50 | | 1.78 | | 1.97 | |

*Osteoarthritis severity rating scale: 1 = better, 2 = no change, 3 = worsened.
**nsd = no significant difference.

Study #2

A canine study was conducted to evaluate the dietary effect of feeding high levels of n-3 fatty acids to dogs diagnosed with osteoarthritis. Two veterinary orthopedic specialists enrolled patients in the study. A total of 38 dogs were randomly assigned to two dietary treatments and fed for 90 days. The test and control diets were manufactured from the same lots of foods as described above (Table 6).

Serum fatty acids, force plate gait analysis, and veterinary clinical assessments were recorded at 0, 45, and 90 days. Serum fatty acid profiles were significantly modulated by the test food. The test group had significantly higher serum concentrations of n-3 fatty acids (P<0.01), specifically EPA, DHA, ALA, significantly lower concentrations of AA at day 90 (P<0.01), and significantly lower n-6:n-3 ratios (P<0.01) as compared to the control group at the conclusion of each feeding interval (Table 9).

TABLE 9*

Canine Serum Fatty Acid Levels (mg/dl)

| Fatty Acids | Group | Day 0 Mean | P Value | Day 45 Mean | P Value | Day 90 Mean | P Value |
|---|---|---|---|---|---|---|---|
| C18:3 n3 (α - ALA) | Control | 0.89 | 0.7764 | 0.34 | <.0001 | 0.27 | <.0001 |
| | Test | 0.98 | | 4.45 | | 5.04 | |
| C20:4 n-6 (AA) | Control | 55.55 | 0.6880 | 50.78 | 0.0736 | 55.95 | 0.0001 |
| | Test | 57.13 | | 41.94 | | 38.01 | |
| C20:5 n-3 (EPA) | Control | 1.19 | 0.7000 | 0.34 | <.0001 | 0.20 | <.0001 |
| | Test | 1.54 | | 11.52 | | 11.89 | |
| C22:6 n-3 (DHA) | Control | 4.30 | 0.4323 | 1.82 | <.0001 | 1.32 | <.0001 |
| | Test | 3.37 | | 11.15 | | 11.21 | |
| Sum n-6 | Control | 122.85 | 0.2508 | 112.46 | 0.0148 | 114.60 | 0.0036 |
| | Test | 113.61 | | 91.72 | | 89.85 | |
| Sum n-3 | Control | 6.36 | 0.8335 | 2.57 | <.0001 | 1.79 | <.0001 |
| | Test | 5.90 | | 27.14 | | 28.13 | |
| n-6:n-3 ratio | Control | 32.54 | 0.2521 | 66.66 | <.0001 | 75.90 | <.0001 |
| | Test | 45.90 | | 8.48 | | 3.59 | |

*ALA = alpha-linolenic acid; AA = arachidonic acid; EPA = eicosapentaenoic acid; DHA = docosahexaenoic acid.*

A biomechanical assessment of the dogs' most severe osteoarthritic limb was objectively evaluated using force plate gait analysis (Table 10). Vertical peak force is the key parameter measured to determine weight bearing of the affected limb. There was no significant change in mean vertical peak force over the duration of the 90 day feeding for the control group (P=0.91), while there was a significant increase in mean vertical peak force over time for the test group (P=0.01). The percent mean change in vertical peak force was also significantly different between groups (P<0.05), indicating that the test group increased weight bearing in the affected limb, while the control group displayed no change in weight bearing over the course of the study. Weight bearing ability can also be represented by displaying the frequency distribution of percent change in vertical peak for each dietary group. Only 31% of animals in the control group showed improvement in weight bearing after the 90 day feeding, while 82% of the dogs in the test group increased weight bearing over the course of the study.

TABLE 10

Vertical Peak Force

| Group | Day 0 Mean | P Value | Day 90 Mean | P Value | Change (Day 0-90) Mean Change | Mean = 0 Pr > 1 t 1 | % Mean Change | Pr > 1 t 1 |
|---|---|---|---|---|---|---|---|---|
| Control | 72.80 | 0.5981 | 72.63 | 0.9323 | −0.17 | 0.9144 | −0.58 | 0.0443 |
| Test | 69.51 | | 73.21 | | 3.71 | 0.0103 | 5.35 | |

The subjective clinical evaluations performed by the veterinary orthopedic surgeons provided additional support for the efficaciousness of the test diet. Based upon the comprehensive veterinary clinical assessment, a significantly greater percent of dogs were evaluated as improved that consumed the test food as compared to dogs that consumed the control food (P<0.05). The veterinary specialists also observed a greater percent of dogs in the test group displaying a reduction in pain on palpation of the joint as compared to the control group (P=0.05).

Study #3

A canine study was conducted to determine the dose effect of feeding high levels of n-3 fatty acids to dogs diagnosed with osteoarthritis. Twenty-eight veterinary general practitioners enrolled patients in the study. A total of 177 dogs were randomly assigned to three dietary treatments and fed for 90 days. Approximately two-thirds of the dogs participating in the study were receiving medications and/or supplements prescribed for treating osteoarthritis, in addition to consuming the therapeutic diets being evaluated. The three test foods had similar macronutrient profiles, but varied in composition of EPA and DHA, with variable A containing the lowest levels and variable C containing the highest levels (Table 11).

TABLE 11*

| Dietary Nutrient | Test Variable % | | |
|---|---|---|---|
| | A | B | C |
| Protein | 19.97 | 19.51 | 19.37 |
| Fat (total) | 13.78 | 15.34 | 19.55 |
| $CHO_2$ (NFE) | 53.92 | 52.34 | 47.66 |
| C18:3 n-3 (ALA) | 2.65 | 1.18 | 1.10 |
| C20:4 n-6 (AA) | 0.11 | 0.18 | 0.24 |
| C20:5 n-3 (EPA) | 0.50 | 1.18 | 1.69 |
| C22:6 n-3 (DHA) | 0.34 | 0.80 | 1.15 |
| Sum n-6 | 2.70 | 2.45 | 2.14 |
| Sum n-3 | 3.54 | 3.53 | 4.52 |
| n6/n3 ratio | 0.76 | 0.7 | 0.47 |

*NFE = Soluble carbohydrate content as Nitrogen Free Extract; ALA = alpha-linolenic acid; AA = arachidonic acid; EPA = eicosapentaenoic acid; DHA = docosahexaenoic acid.

Serum fatty acids, pet owner evaluations, and veterinary clinical assessments were recorded at 0, 21, 45, and 90 days. Serum fatty acid profiles were significantly modulated by all dietary variables. The dogs fed test variables B & C had significantly higher serum concentrations of n-3 fatty acids (P<0.01), specifically EPA, DHA, ALA, significantly lower concentrations of n-6 fatty acids, specifically AA (P<0.01), and significantly lower n-6:n-3 ratios (P<0.01) as compared to the dogs feed test variable A at the conclusion of each feeding interval (Table 12).

TABLE 12*

Canine Serum Fatty Acid Levels (mg/dl)

| Fatty Acids | Group | Day 0 Mean | Day 21 Mean | Day 45 Mean | Day 90 Mean |
|---|---|---|---|---|---|
| C18:3 n-3 (ALA) | A | 1.34 | 5.65 | 5.29 | 5.63 |
| | B | 1.29 | 3.36 | 3.99 | 3.82 |
| | C | 1.25 | 2.92 | 3.32 | 3.29 |
| C20:4 n-6 (AA) | A | 76.37 | 51.10 | 47.54 | 47.77 |
| | B | 73.15 | 41.55 | 38.94 | 37.0 |
| | C | 70.05 | 37.35 | 36.86 | 34.73 |
| C20:5 n-3 (EPA) | A | 1.32 | 18.74 | 18.51 | 19.26 |
| | B | 1.54 | 26.14 | 29.87 | 30.03 |
| | C | 1.85 | 34.42 | 35.71 | 39.04 |
| C22:6 n-3 (DHA) | A | 3.50 | 13.75 | 13.84 | 13.88 |
| | B | 4.72 | 18.47 | 19.98 | 20.16 |
| | C | 3.91 | 21.01 | 21.47 | 22.49 |
| Sum n-6 | A | 150.38 | 114.38 | 110.12 | 112.70 |
| | B | 143.93 | 93.83 | 95.87 | 92.10 |
| | C | 139.97 | 79.71 | 82.65 | 80.74 |
| Sum n-3 | A | 6.16 | 38.14 | 37.65 | 38.77 |
| | B | 7.55 | 47.96 | 53.84 | 54.01 |
| | C | 7.01 | 58.35 | 60.50 | 68.83 |
| n-6:n-3 ratio | A | 29.99 | 5.65 | 3.48 | 3.75 |
| | B | 28.09 | 3.36 | 1.92 | 1.79 |
| | C | 32.30 | 2.92 | 2.02 | 1.73 |

*ALA = alpha-linolenic acid; AA = arachidonic acid; EPA = eicosapentaenoic acid; DHA = docosahexaenoic acid.

Pet owners reported improvements in 13 of 14 individual osteoarthritic signs for dogs consuming any of the dietary variables for 21 days (Table 13). Additionally, pet owners reported a decrease in severity for 13 of 14 individual osteoarthritic signs for dogs consuming any of the dietary variables for 90 days (Table 14). Pet owners also reported a significant reduction in the frequency of observable osteoarthritic signs after the dogs consumed any of the dietary variables for 90 days (Table 15).

TABLE 13

Pet Owner Observed Improvements in Osteoarthritic Signs (Day 0-21)

| Osteoarthritic Sign | Diet | Mean | Mean = 0 Pr > 1 t 1 |
|---|---|---|---|
| Rising from rest | A | −0.439 | 0.0002 |
| | B | −0.738 | <.0001 |
| | C | −0.763 | <.0001 |
| Limping | A | −0.720 | <.0001 |
| | B | −0.731 | <.0001 |
| | C | −0.837 | <.0001 |

TABLE 13-continued

Pet Owner Observed Improvements in Osteoarthritic Signs (Day 0-21)

| Osteoarthritic Sign | Diet | Mean | Mean = 0 Pr > \|t\| |
|---|---|---|---|
| Stiffness | A | −0.537 | <.0001 |
|  | B | −0.783 | <.0001 |
|  | C | −0.627 | <.0001 |
| Soreness | A | −0.750 | 0.0005 |
|  | B | −0.800 | 0.0002 |
|  | C | −0.379 | 0.0451 |
| Lagging behind on walks | A | −0.564 | 0.0004 |
|  | B | −0.909 | <.0001 |
|  | C | −0.531 | 0.0022 |
| Pain | A | −0.476 | 0.0245 |
|  | B | −0.478 | 0.0184 |
|  | C | −0.889 | 0.0002 |
| Aggression | A | 0.000 | 1.0000 |
|  | B | −0.313 | 0.1050 |
|  | C | −0.429 | 0.1401 |
| Running | A | −0.524 | 0.0004 |
|  | B | −0.682 | <.0001 |
|  | C | −0.674 | <.0001 |
| Walking | A | −0.553 | 0.0007 |
|  | B | −0.750 | <.0001 |
|  | C | −0.667 | <.0001 |
| Stair Climbing | A | −0.449 | 0.0012 |
|  | B | −0.667 | <.0001 |
|  | C | −0.723 | <.0001 |
| Jumping | A | −0.362 | 0.0049 |
|  | B | −0.600 | <.0001 |
|  | C | −0.542 | <.0001 |
| Playing | A | −0.622 | <.0001 |
|  | B | −0.763 | <.0001 |
|  | C | −0.487 | 0.0014 |
| Impaired Mobility | A | −0.528 | 0.0005 |
|  | B | −0.700 | <.0001 |
|  | C | −0.564 | 0.0001 |
| Activity Level | A | −0.745 | <.0001 |
|  | B | −0.857 | <.0001 |
|  | C | −0.865 | <.0001 |

The above "p" values refer to the mean change from day 0 to day 21.

TABLE 14

Difference in Pet Owners Severity Rating (day 0-90)

| Osteoarthritic Sign | Group | Mean | Pr > t |
|---|---|---|---|
| Rising from rest | A | −0.463 | <.0001 |
|  | B | −0.633 | <.0001 |
|  | C | −0.518 | <.0001 |
| Limping | A | −0.489 | 0.0003 |
|  | B | −0.588 | <.0001 |
|  | C | −0.681 | <.0001 |
| Stiffness | A | −0.255 | 0.0420 |
|  | B | −0.483 | <.0001 |
|  | C | −0.589 | <.0001 |
| Soreness | A | −0.810 | <.0001 |
|  | B | −0.920 | <.0001 |
|  | C | −0.926 | <.0001 |
| Lagging behind on walks | A | −0.657 | <.0001 |
|  | B | −0.531 | 0.0014 |
|  | C | −0.448 | 0.0094 |
| Pain | A | −0.684 | 0.0002 |
|  | B | −0.571 | 0.0009 |
|  | C | −0.667 | 0.0010 |
| Aggression | A | −0.750 | 0.0234 |
|  | B | −1.000 | 0.0025 |
|  | C | −1.000 | 0.0751 |
| Running | A | −0.579 | <.0001 |
|  | B | −0.558 | <.0001 |
|  | C | −0.605 | <.0001 |
| Walking | A | −0.294 | 0.0358 |
|  | B | −0.643 | <.0001 |
|  | C | −0.595 | <.0001 |
| Stair Climbing | A | −0.419 | 0.0024 |
|  | B | −0.489 | 0.0002 |
|  | C | −0.689 | <.0001 |
| Jumping | A | −0.571 | 0.0003 |
|  | B | −0.479 | 0.0011 |
|  | C | −0.773 | <.0001 |
| Playing | A | −0.606 | 0.0002 |
|  | B | −0.571 | 0.0003 |
|  | C | −0.694 | <.0001 |
| Lameness | A | −0.484 | 0.0045 |
|  | B | −0.778 | <.0001 |
|  | C | −0.667 | <.0001 |
| Activity Level | A | −0.409 | 0.0009 |
|  | B | −0.704 | <.0001 |
|  | C | −0.551 | <.0001 |

The above "p" values refer to the mean change from day 0 to day 90.

Dogs consuming higher concentrations of n-3 fatty acids were reported to have more significant improvement in osteoarthritic condition and more significant reduction in the progression of osteoarthritis than those dogs receiving the lowest dosage, based on veterinarians clinical assessments (Table 16). There was no significant difference in improvement in osteoarthritic condition or reduction in the progression of osteoarthritis between the group receiving medications and/or supplements and the non-medicated group (Table 17). This indicates that the therapeutic diets work synergistically with other therapies or at least not withstanding other therapies by providing additional benefit to dogs suffering from osteoarthritis.

An extremely low incidence of adverse reactions or side effects were reported among dogs participating in this study. Only five dogs out of the 215 animals assigned to food were reported to have diarrhea and vomiting, which could possibly be attributed to consuming one of dietary variables. Similar incidence of adverse reactions or side effects were reported for those dogs consuming the therapeutic diets in the previous two studies discussed (1/88 and 1/26 for examples 1 and 2 respectively.

TABLE 15

Difference in Pet Owners Frequency Rating (day 0-90)

| Osteoarthritic Sign | Group | Mean | Pr > t |
|---|---|---|---|
| Rising from rest | A | −0.370 | <.0001 |
|  | B | −0.467 | <.0001 |
|  | C | −0.509 | <.0001 |
| Stiffness | A | −0.098 | 0.2929 |
|  | B | −0.373 | <.0001 |
|  | C | −0.421 | <.0001 |
| Soreness | A | −0.381 | 0.0146 |
|  | B | −0.680 | <.0001 |
|  | C | −0.821 | <.0001 |
| Running | A | −0.447 | 0.0004 |
|  | B | −0.395 | 0.0009 |
|  | C | −0.477 | <.0001 |
| Jumping | A | −0.357 | 0.0027 |
|  | B | −0.354 | 0.0015 |
|  | C | −0.467 | <.0001 |
| Playing | A | −0.455 | 0.0013 |
|  | B | −0.297 | 0.0238 |
|  | C | −0.667 | 0.0010 |
| Limping | A | −0.239 | <.0165 |
|  | B | −0.365 | <.0001 |
|  | C | −0.396 | <.0001 |

TABLE 15-continued

Difference in Pet Owners Frequency Rating (day 0-90)

| Osteoarthritic Sign | Group | Mean | Pr > t |
|---|---|---|---|
| Lagging | A | −0.571 | <.0001 |
| Behind on | B | −0.643 | <.0001 |
| Walks | C | −0.500 | 0.0004 |
| Aggression | A | −0.417 | 0.0536 |
| | B | −0.467 | 0.0175 |
| | C | −0.167 | 0.5741 |
| Walking | A | −0.206 | 0.0911 |
| | B | −0.558 | <.0001 |
| | C | −0.447 | 0.0002 |
| Stair Climbing | A | −0.302 | 0.0069 |
| | B | −0.348 | 0.0014 |
| | C | −0.457 | <.0001 |
| Impaired | A | −0.250 | 0.0643 |
| Mobility | B | −0.436 | 0.0005 |
| | C | −0.667 | <.0001 |

TABLE 16

| Diet | N | Mean | P | |
|---|---|---|---|---|
| Progression of Osteoarthritic Condition | | | | |
| A | 55 | 2.327 | 0.2891 | A vs B |
| B | 62 | 2.177 | 0.1619 | B vs C |
| C | 59 | 1.983 | 0.0168 | A vs C |
| Overall Change in Osteoarthritic Condition | | | | |
| A | 54 | 3.148 | 0.1675 | A vs B |
| B | 62 | 2.871 | 0.0787 | B vs C |
| C | 59 | 2.525 | 0.0024 | A vs C |

TABLE 17

| Diet | Medicated | N | Mean | P |
|---|---|---|---|---|
| Progression of Osteoarthritic Condition | | | | |
| A | No | 22 | 2.273 | 0.6665 |
| A | Yes | 33 | 2.364 | |
| B | No | 23 | 2.130 | 0.7109 |
| B | Yes | 39 | 2.205 | |
| C | No | 28 | 2.071 | 0.4003 |
| C | Yes | 31 | 1.903 | |
| Overall Change in Osteoarthritic Condition | | | | |
| A | No | 21 | 3.143 | 0.9770 |
| A | Yes | 33 | 3.152 | |
| B | No | 23 | 2.696 | 0.3247 |
| B | Yes | 39 | 2.974 | |
| C | No | 28 | 2.750 | 0.1285 |
| C | Yes | 31 | 2.323 | |

All references cited in this specification are hereby incorporated by reference. Any discussion of references cited herein is intended merely to summarize the assertions made by their authors and no admission is made that any reference or portion thereof constitutes relevant prior art. Applicants reserve the right to challenge the accuracy and pertinence of the cited references.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for restoring joint function in a dog having osteoarthritis, the method comprising administering a joint-function restoring amount of eicosapentaenoic acid (EPA) to the dog in need thereof, the administering comprising feeding to the dog a diet comprising eicosapentaenoic acid (EPA) at a concentration within a range of from about 0.4% to about 5.0% by weight, a total omega-3 fatty acid content within a range of from about 3.5% to about 8.0% by weight on a dry matter basis, and at least one of an omega-6 fatty acid, wherein the ration of total omega-3 fatty acids to total omega-6 fatty acids in the diet is 1 total omega-3 fatty acids to about 0.2 total omega-6 fatty acids, and wherein said diet is effective to restore joint function in said dog.

2. A method according to claim 1, wherein the diet comprises eicosapentaenoic acid (EPA) at a concentration of at least about 0.5% by weight.

3. A method according to claim 1, wherein the diet further comprises arachidonic acid, wherein the ratio of arachidonic acid to eicosapentaenoic acid is about 0.28 to about 0.01 arachidonic acid to 1 eicosapentaenoic acid.

4. A method as in one of claims 1, 2, or 3, wherein the diet comprises omega-6 fatty acids at a concentration of about 3% by weight or less.

5. A method of treating osteoarthritis in a dog, the method comprising administering to an osteoarthritic dog in need thereof a dietary composition comprising eicosapentaenoic acid (EPA) at a concentration within a range of from about 0.4% to about 5.0% by weight, and a total omega-3 fatty acid content within a range of from about 3.5% to about 8.0% by weight on a dry matter basis, wherein the ratio of total omega-3 fatty acids to omega-6 fatty acids is at least about 1 total omega-3 fatty acids to about 0.8 to about 0.2 total omega-6 fatty acids.

6. A method of treating osteoarthritis in a dog, the method comprising administering to an osteoarthritic dog in need thereof a dietary composition comprising eicosapentaenoic acid (EPA) at a concentration within a range of from about 0.4% to about 5.0% by weight, and a total omega-3 fatty acid content within a range of from about 3.5% to about 8.0% and a total omega-6 fatty acid content of about 3 wt. % or lower on a dry matter basis, wherein the ratio of total omega-3 fatty acids to omega-6 fatty acids is at least about 1 total omega-3 fatty acids to about 0.8 to about 0.2 total omega-6 fatty acids.

7. A method of treating osteoarthritis in a dog, the method comprising administering to an osteoarthritic dog in need thereof a dietary composition comprising eicosapentaenoic acid (EPA) at a concentration within a range of from about 0.4% to about 5.0% by weight, and a total omega-3 fatty acid content within a range of from about 3.5% to about 8.0% by weight on a dry matter basis, wherein the ratio of total omega-3 fatty acids to omega-6 fatty acids is at least about 1 total omega-3 fatty acids to about 0.8 to about 0.2 total omega-6 fatty acids and wherein the ratio of arachidonic acid (AA) to eicosapentaenoic (EPA) is about 0.28 to about 0.01 arachidonic acid to 1 eicosapentaenoic acid (EPA).

8. A method of treating osteoarthritis in a dog, the method comprising administering to an osteoarthritic dog in need thereof a dietary composition comprising eicosapentaenoic acid (EPA) at a concentration within a range of from about 0.4% to about 5.0% by weight, and a total omega-3 fatty acid content within a range of from about 3.5% to about 8.0% and a total omega-6 fatty acid content of about 3 wt. % or lower on a dry matter basis, wherein the ratio of total omega-3 fatty acids to omega-6 fatty acids is at least about 1 total omega-3 fatty acids to about 0.8 to about 0.2 total omega-6 fatty acids and wherein the ratio of arachidonic acid (AA) to eicosapentaenoic (EPA) is about 0.28 to about 0.01 arachidonic acid to 1 eicosapentaenoic acid (EPA).

9. The method as in one of claims 5, 6, 7 or 8, wherein the amount of eicosapentaenoic acid (EPA) administered to said osteoarthritic dog is at least about 55 mg of eicosapentaenoic acid per kg body weight per day.

10. The method as in one of claims 5, 6, 7 or 8, wherein said composition is selected from the group consisting of a dietary composition, a snack, a dietary supplement or a pet treat.

11. The method as in one of claims 5, 6, 7 or 8, wherein said composition is a dry dietary composition.

12. The method as in one of claims 5, 6, 7 or 8, wherein said composition is a wet dietary composition.

13. The method as in one of claims 5, 6, 7 or 8, wherein said composition comprises eicosapentaenoic acid (EPA) at a concentration of at least about 0.5 wt. %.

* * * * *